(12) United States Patent
Neumann

(10) Patent No.: US 11,211,158 B1
(45) Date of Patent: Dec. 28, 2021

(54) SYSTEM AND METHOD FOR REPRESENTING AN ARRANGED LIST OF PROVIDER ALIMENT POSSIBILITIES

(71) Applicant: KPN INNOVATIONS, LLC., Lakewood, CO (US)

(72) Inventor: Kenneth Neumann, Lakewood, CO (US)

(73) Assignee: KPN INNOVATIONS, LLC., Lakewood, CO (US)

(*) Notice: Subject to any disclaimer, the term of this patent is extended or adjusted under 35 U.S.C. 154(b) by 0 days.

(21) Appl. No.: 17/007,318

(22) Filed: Aug. 31, 2020

(51) Int. Cl.
*G16H 20/60* (2018.01)
*G16H 50/30* (2018.01)
*G16H 50/70* (2018.01)
*G16H 50/20* (2018.01)

(52) U.S. Cl.
CPC .............. *G16H 20/60* (2018.01); *G16H 50/20* (2018.01); *G16H 50/30* (2018.01); *G16H 50/70* (2018.01)

(58) Field of Classification Search
CPC ........ G16H 20/60; G16H 50/30; G16H 50/70; G16H 50/20
See application file for complete search history.

(56) References Cited

U.S. PATENT DOCUMENTS

| | | |
|---|---|---|
| 8,271,415 B2 | 9/2012 | Iliff |
| 8,370,070 B2 | 2/2013 | Fernandez |
| 8,532,938 B2 | 9/2013 | Jung et al. |
| 8,697,370 B2 | 4/2014 | Kas et al. |
| 8,762,167 B2 | 6/2014 | Blander et al. |
| 9,120,852 B2 | 9/2015 | Jouhanneaud |
| 9,207,242 B2 | 12/2015 | Luk et al. |

(Continued)

FOREIGN PATENT DOCUMENTS

| | | |
|---|---|---|
| WO | 2008058399 | 5/2008 |
| WO | 1904006347 | 1/2014 |

(Continued)

OTHER PUBLICATIONS

MagMAX CORE Nucleic Acid Purification Kit, Flyer, 2019, ThermoFisher Scientific.

*Primary Examiner* — Mohamed Charioui
*Assistant Examiner* — Christine Y Liao
(74) *Attorney, Agent, or Firm* — Caldwell Intellectual Property Law, LLC

(57) ABSTRACT

A system for representing an arranged list of alimentary aliment possibilities includes a computing device configured to receive an input of an autoimmune disorder, identify a marker associated with the autoimmune disorder, generate a marker classifier, wherein the marker classifier out puts a disorder state label, determine an aliment instruction set including a plurality of edible programs corresponding to a plurality of provider alimentary possibilities, locate, from each alimentary provider device of a plurality of alimentary provider devices, a plurality of provider aliment possibilities, generate an arranged list of edible programs as a function of the plurality of provider aliment possibilities, obtain a user preference of a provider aliment possibility corresponding to an edible of the plurality of provider alimentary possibilities, and generate a updated arranged list of alimentary possibilities as a function of the user preference and the aliment instruction set.

20 Claims, 9 Drawing Sheets

(56) References Cited

U.S. PATENT DOCUMENTS

| | | | |
|---|---|---|---|
| 2002/0019749 A1* | 2/2002 | Becker | G16H 70/20 |
| | | | 705/2 |
| 2004/0122787 A1 | 6/2004 | Avinash et al. | |
| 2008/0103831 A1* | 5/2008 | Spiotta | G06Q 50/24 |
| | | | 705/3 |
| 2010/0267052 A1 | 10/2010 | Gelber et al. | |
| 2011/0230733 A1 | 9/2011 | Al-Ali | |
| 2014/0310019 A1 | 10/2014 | Blander et al. | |
| 2015/0079033 A1 | 3/2015 | Shuber et al. | |
| 2015/0252436 A1 | 9/2015 | Samant et al. | |
| 2016/0068916 A1 | 3/2016 | Nekarda et al. | |
| 2016/0224748 A1* | 8/2016 | Apte | G16B 40/00 |
| 2016/0367188 A1 | 12/2016 | Malik et al. | |
| 2018/0032698 A1 | 2/2018 | Lau et al. | |
| 2018/0106807 A1 | 4/2018 | Redston | |
| 2018/0306804 A1 | 10/2018 | Micallef et al. | |
| 2019/0025333 A1 | 1/2019 | Zhang et al. | |
| 2019/0065670 A1* | 2/2019 | Yandell | G16B 50/00 |
| 2019/0074080 A1 | 3/2019 | Appelbaum et al. | |
| 2019/0078142 A1 | 3/2019 | Apte et al. | |
| 2019/0087536 A1 | 3/2019 | Apte et al. | |

FOREIGN PATENT DOCUMENTS

| | | |
|---|---|---|
| WO | 2014071455 | 5/2014 |
| WO | 2015085368 | 6/2015 |
| WO | 2017044885 | 3/2017 |
| WO | 2017044902 | 3/2017 |
| WO | 2018020239 | 2/2018 |

* cited by examiner

SYSTEM AND METHOD FOR REPRESENTING AN ARRANGED LIST OF PROVIDER ALIMENT POSSIBILITIES

FIELD OF THE INVENTION

The present invention generally relates to the field of network communication and processing. In particular, the present invention is directed to a system and method for representing an arranged list of provider aliment possibilities

BACKGROUND

Current alimentary design systems can be challenged to modify the nutritional delivery based on current or future user autoimmune disorders. This leads to an inefficient edible delivery system and a poor nutrient edible program. The current invention disclosed provides an optimized nutrient delivery system through a machine-learning process to aid in preventing or treating user autoimmune disorders.

SUMMARY OF THE DISCLOSURE

In an aspect, a system for representing an arranged list of provider aliment possibilities, the system comprising a computing device, the computing device designed and configured to receive an input representing an autoimmune disorder; identify a marker of the user, wherein identifying the marker of the user comprises comparing the represented autoimmune disorder to a list of autoimmune disorders stored with an autoimmune data bank, wherein each autoimmune disorder in the list of autoimmune disorders is associated with a respective marker; and identify the marker of the user as a function of the comparison of the represented autoimmune disorder to the list of autoimmune disorders; generate a marker classifier, the marker classifier trained using a first training set correlating each of a plurality of markers to a respective disorder state label and configured to receive the identified marker of the user and output a disorder state label as a function of the first training data; determine, as a function of the disorder state label, an aliment instruction set containing an edible program, wherein determining further comprises generating an aliment machine-learning process, the aliment machine-learning process trained by a second training set correlating each of a plurality of disorder state labels to a respective aliment instruction set and configured to receive the disorder state label as an input and output the edible program as a function of the second training data; and generate an arranged list of provider aliment possibilities from a plurality of aliment possibilities as a function of the aliment instruction set; and represent the arranged list on a display.

In an aspect, a method of representing an arranged list of provider aliment possibilities, the method comprising receiving, by a computing device, an input representing an autoimmune disorder; identifying, by the computing device, a marker of the user, wherein identifying the marker of the user comprises comparing the represented autoimmune disorder to a list of autoimmune disorders stored with an autoimmune data bank, wherein each autoimmune disorder in the list of autoimmune disorders is associated with a respective marker; and identifying the marker of the user as a function of the comparison of the represented autoimmune disorder to the list of autoimmune disorders; generating, by the computing device, a marker classifier, the marker classifier trained using a first training set correlating each of a plurality of markers to a respective disorder state label and configured to receive the identified marker of the user and output a disorder state label as a function of the first training data; determining, by the computing device, as a function of the disorder state label, an aliment instruction set containing an edible program, wherein determining further comprises generating an aliment machine-learning process, the aliment machine-learning process trained by a second training set correlating each of a plurality of disorder state labels to a respective aliment instruction set and configured to receive the disorder state label as an input and output the edible program as a function of the second training data; and generating, by the computing device, an arranged list of provider aliment possibilities from a plurality of aliment possibilities as a function of the aliment instruction set; and representing, by the computing device, the arranged list on a display.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for arranging a list of provider aliment possibilities. In an embodiment, this system provides alimentary possibilities for a plurality of autoimmune disorders as a function of the edible programs required. Edible programs may include recommendations based on user autoimmune disorders. In an embodiment this system can be used to guide a user in the selection of alimentary possibilities as a function of classified markers to generate an aliment instruction set. Aspects of the present disclosure allow for alimentary possibilities that may aid in preventative or therapeutic impacts of a user autoimmune disorder due to target nutrients being delivered. Exemplary embodiments illustrating aspects of the present disclosure are described below in the context of several specific examples.

Figure 1:
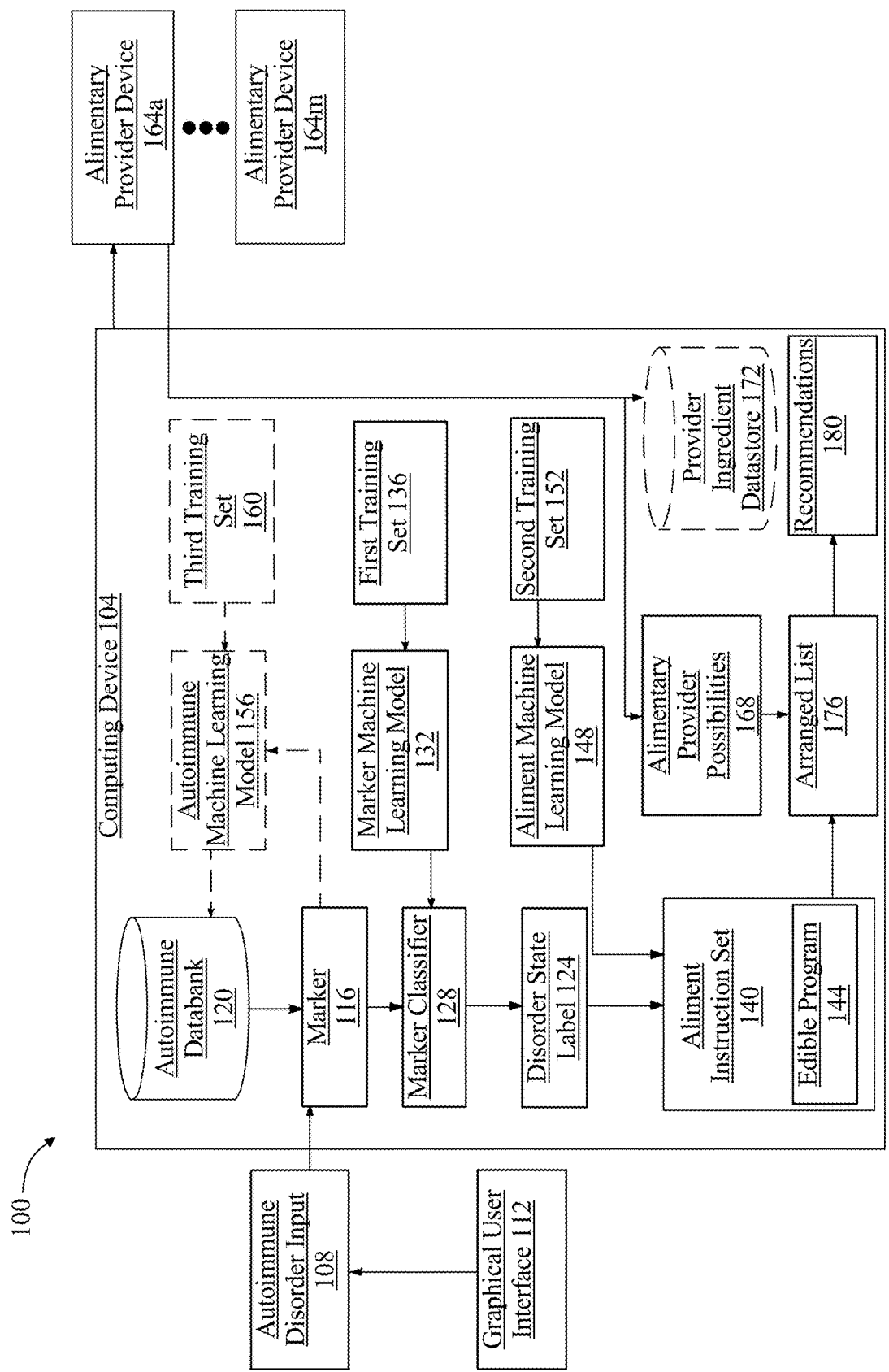
FIG. 1 is a block diagram illustrating a system for representing an arranged list of provider aliment possibilities.

Referring now to FIG. 1, an exemplary embodiment of a system 100 for representing an arranged list of provider aliment possibilities is illustrated. System 100 includes a computing device 104. Computing device 104 may include any computing device as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any possibilities thereof. A network may employ a wired and/or a wireless mode of communication. In general, any network topology may be used. Information (e.g., data, software etc.) may be communicated to and/or from a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device.

With continued reference to FIG. 1 computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, computing device 104 receives an input representing an autoimmune disorder 108. As used in this disclosure an "autoimmune disorder" is the identification and/or selection of an ailment that affects and/or has a likelihood of causing a human body's immune system to attack and/or destroy healthy body tissues by mistake. An autoimmune disorder may include, but is not limited to diabetes, celiac disorder, inflammatory bowel syndrome, systemic lupus erythematosus, Sjogren's syndrome, multiple sclerosis, polymyalgia rheumatica, ankylosing spondylitis, alopecia areata, vasculitis, temporal arteritis, psoriasis, Guillain-Barre syndrome, aplastic anemia, chronic inflammatory demyelinating polyneuropathy, rheumatoid arthritis, and the like. A user may enter an autoimmune disorder within computing device 104. In an embodiment, computing device 104 may include a graphical user interface 112 that may allow for a user to specify an autoimmune disorder input 108. Graphical user interface 112 may include without limitation, a form or other graphical element having display fields, where one or more elements of information may be displayed. Graphical user interface 112 may include sliders that a user may adjust to indicate the one or more autoimmune conditions the user may have been previously diagnosed with. In an embodiment, graphical user interface 112 may include free form textual entries, where a user may type in information regarding an autoimmune disorder input 108. In an embodiment, graphical user interface 112 may display a series of questions to prompt a user for information pertaining to an autoimmune disorder input 108. A user may enter one or more subsequent autoimmune disorders indicating to the computing device 104 that one or more additional autoimmune disorders are present. As a further example, computing device 104 may display a list of autoimmune disorders to user, from which user may select an autoimmune disorder the user currently suffers from. List may be presented, without limitation, in rank order to user. As used in this disclosure "a rank order" is a list of autoimmune disorders currently effecting society ranked based on the prevalence in society from most prevalent to least prevalent based on current scientific literature. Computing device 104 may receive user selection of a user autoimmune disorders and select additional autoimmune disorders as a function of the user selection. Alternatively or additionally, a highest-ranking autoimmune disorder and/or a list of highest-ranking autoimmune disorders, based on prevalence, may be presented to user for user to select or reject by way of a user entry; rejection of one autoimmune disorder so displayed may cause computing device 104 to display a next highest-ranking autoimmune disorder to user, which may be repeated iteratively until user selects a listed autoimmune disorder and/or enters an autoimmune disorder by other means. Computing device 104 may present additional autoimmune disorders that the user may accept or reject based on the user selection or user input. For example, a user may select or input an autoimmune disorder of inflammatory bowel syndrome, whereby computing device may generate a list of additional autoimmune disorders correlating to the initial autoimmune disorder selected or inputted, such as celiac disorder. Additional autoimmune disorders may be arranged according to the degree of correlation with the initial user input or selection, whereby computing device 104 may display to user a next highest-ranking autoimmune disorder associated with the current user autoimmune disorder. User selection of remaining correlated autoimmune disorders may then be accepted or rejected by the user. Receiving user autoimmune disorders, and/or ranking of autoimmune disorders, may be implemented, without limitation, as described in U.S. Nonprovisional application Ser. No. 16/890,686, filed on Jun. 2, 2020 and entitled "ARTIFICIAL INTELLIGENCE METHODS AND SYSTEMS FOR CONSTITUTIONAL ANALYSIS USING OBJECTIVE FUNCTIONS" the entirety of which is incorporated herein by reference.

Still referring to FIG. 1 computing device 104 is configured to identify a marker 116 associated with the user. As used in this disclosure, a "marker" is a measurable substance and/or element of physiological data in a human subject whose presence is indicative of some metabolomic state such as disease, infection, state of health of one or more systems within a human body, and/or degree of efficacy of immune system. For example, Interleukin-15 may be a marker for celiac disorder. Interleukin-15 may be found in a biological extraction of a user, which may indicate to computing system 104 the presence of celiac disorder. At least a marker may include, without limitation, hemoglobin A1c (HbA1c), red blood cell magnesium, serum magnesium, complete blood count, red blood cell count, white blood cell count, vitamin D, ferritin, cortisol, high sensitivity C reactive protein (hsCRP), alanine aminotransferase (ALT), glucose, hemoglobin A1c, DHEAS, and/or testosterone. A metabolomic state may include for example, any chemical process occurring inside of a human body that generates small marker metabolites. For example, a metabolomic state may include a chemical signature as a result from an autoimmune disorder such as diabetes, which may generate unique metabolites, chemical signatures, such as acetone in the breath of these individuals. Additionally or alternatively, the autoimmune disorder input of diabetes may be entered in the computing device, which may cause computing system 104 to identify a marker associated with diabetes such as a blood glucose level. One or more markers associated with an input of autoimmune disorder 108 may be identified for the user. Marker 116, having an association with autoimmune disorder input 108 may or may not be currently present in the user and/or may contain a positive and/or negative result. In an embodiment, a marker 116 may be associated with one or more autoimmune disorder inputs 108. For instance, and without limitation, a marker such as erythrocyte sedimentation rate (ESR) may be associated with several autoimmune disorder inputs 108, including but not limited to rheumatoid arthritis, and systemic lupus erythematosus. Information pertaining to marker 116 and/or autoimmune disorder input 108 may be stored within an autoimmune databank 120. Autoimmune databank 120 may be implemented, without limitation, as a relational database, a key-value retrieval datastore such as a NOSQL database, or any other format or structure for use as a datastore that a person skilled in the art would recognize as suitable upon review of the entirety of this disclosure. Autoimmune databank 120 may be generated from a plurality of sources as discussed below. Persons skilled in the art, upon reviewing the entirety of this disclosure, will be aware of various markers associated with a plurality of autoimmune disorders.

With continued reference to FIG. 1, computing device 104 may be configured to display an autoimmune disorder on graphical user interface 112 as a function of marker 116. Autoimmune disorder may be identified through a biological extraction of the user and correlated to marker 116, which is marker 116 of autoimmune disorder. Autoimmune disorder may then be inputted to autoimmune database 120 and computing system 104 may identify additional markers 116 associated with autoimmune disorder. Additionally or alternatively, another example may be during a physician examination a marker may be present that may indicate the presence of autoimmune disorder. For example, a physician may indicate the presence of blood in the stool of a user. This marker may then be used to determine the presence of inflammatory bowel disorder in the user, which may indicate to computer system 104 the user input of inflammatory bowel disorder. A marker may alternatively or additionally include measures of microbiome, physiological markers such as heart rate variability, pulse, pressure, body mass index, and/or any other element of physiological data and/or biological extraction, for instance as described in U.S. Nonprovisional application Ser. No. 16/659,817, filed on Oct. 22, 2019, and entitled "METHODS AND SYSTEMS FOR IDENTIFYING COMPATIBLE MEAL OPTIONS," the entirety of which is incorporated herein by reference.

With continued reference to FIG. 1 computing device 104 is configured to generate a marker classifier 128, wherein marker classifier 128 identifies a set impact value associated with an autoimmune disorder. Computing device 104 is configured to generate marker classifier 128, where marker classifier 128 is trained using a first training set correlating each of a plurality of markers to a respective disorder state label and configured to receive the identified marker of a user and output a disorder state label as a function of first training data. Marker classifier 128 uses an identified marker of a user as an input, and outputs a disorder state label. Additionally or alternatively, marker classifier 128 may be generated using a marker machine learning model 132. Marker machine learning model 132 may include machine learning algorithms including, algorithms such as, simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve Bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, markov decision processes, or Deep Deterministic Policy Gradient (DDPG) machine learning algorithms to generate the marker classifier 128 quantitative value, see FIG. 2 below for further details regarding machine learning models. Marker machine learning model 132 may be generated as a function of a first training set 136. First training set 136 may include, without limitation, markers such as proteins, cells, vitamins, electrolytes, or chemicals present in a user that indicate a predisposition for developing autoimmune disorder in the future. For example, a marker of a plurality of markers such may be glucose in the user, which may indicate the active autoimmune disorder for diabetes. Another example may be markers 116 such as chitinase 3-like 1 (cartilage glycoprotein-39) (CH13L1); C reactive protein, pentraxin-related (CRP); epidermal growth factor (beta-urogastrone) (EGF); interleukin 6 (interferon, beta 2) (IL6); leptin (LEP); matrix metallopeptidase 1 (interstitial collagenase) (MMP1); matrix metallopeptidase 3 (stromelysin 1, progelatinase) (MMP3); resistin (RETN); serum amyloid A1 (SAA1); tumor necrosis factor receptor superfamily, member 1A (TNFRSF1A), vascular cell adhesion molecule 1 (VCAM1); and, vascular endothelial growth factor A (VEGFA), which may be present in a user as a function of a likelihood to develop rheumatoid arthritis. Computing system 104 generates a disorder state label 124 as a function of marker classifier 128. As used in this disclosure a "disorder state label" is a quantitative measure of a marker classifier 128 that identifies the likelihood for an autoimmune disorder or an active autoimmune disorder as function of the quantitative value. For example, Interleukin-15 may have an impact value of 10, indicating a strong propensity for the autoimmune disorder celiac disorder, while the marker vitamin D may have an impact value of 0, indicating no likelihood for the presence of celiac disorder. Disorder state label is generated as a function of marker classifier 128 such that if a certain quantitative threshold is established the disorder state label may determine if the individual has a likelihood for an autoimmune disorder or may have an active autoimmune disorder.

With continued reference to FIG. 1, computing device 104 identifies a marker of a user by comparing a represented autoimmune disorder to a list of autoimmune disorders stored within an autoimmune data bank, wherein each autoimmune disorder in the list of autoimmune disorders is associated with a respective marker. In an embodiment, a list may include a compilation of each autoimmune disorder, and each associated respective marker. Information contained within a list may be based upon one or more expert inputs such as medical doctors, scientists, medical literature, journal articles, and the like. Computing device 104 identifies a marker of a user as a function of comparing a represented autoimmune disorder to a list of autoimmune disorders. For example, an autoimmune disorder such as multiple sclerosis may be compared to multiple sclerosis contained within the list, whereby respective markers associated with multiple sclerosis may include but are not limited to endothelin-1, creatine, uric acids, CD46, interleukin-10, platelets, and the like.

With continued reference to FIG. 1, computing device 104 is configured to determine an aliment instruction set 140 containing an edible program 144, as a function of disorder state label 124. As used in this disclosure an "aliment instruction set" is a list or other collection of nutritional recommendations for a user, including recommendations of foods, nutrients, ingredients, and/or quantities thereof, that a user should consume to prevent or treat the effects of an autoimmune disorder. Aliment instruction set 140 determines edible program 144. As used in this disclosure, an "edible program" is a quantity of edibles that provide necessary nutrients or ingredients that that aliment instruction set 140 recommends user to consume for preventing or treating a user autoimmune disorder over a subject period. Aliment instruction set may generate a mutable edible program, treatment edible program, or preventative edible program as a function of the disorder state label 124 and the plurality of provider aliment program. For example, a mutable edible program may aid in reversing an autoimmune disorder such as through the edible program containing curcumin, which may reverse the autoimmune disorder multiple sclerosis, while a treatment edible program may be through the delivery of salmon for the treatment of inflammatory disorder. Additionally or alternatively, an edible program containing high vitamin D, such as those described above may be recommended for the preventative treatment of diabetes. As used in this disclosure, a "subject period" may consist of a set time period such as a day, a week, a month, and the like thereof. Edible programs may include numbers representing a maximal amount of one edible to be consumed, a minimal amount of a secondary edible to be consumed, and/or a precise number of additional edibles that may be determined to be ideal. A quantity may be zero for an edible that may be harmful to a user with an autoimmune disorder or may have no positive health benefit to a user with an autoimmune disorder. For example, a user who has diabetes may be recommended a quantity of zero for glucose, sucrose, fructose, or the like thereof.

With continued reference to FIG. 1, computing device 104 determines aliment instruction set 140, as a function of an aliment machine learning model 148. Aliment machine learning model may include machine learning algorithms including, but not limited to supervised machine learning, unsupervised machine learning, and reinforcement machine learning. For example, aliment machine learning model may utilize, without limitation, algorithms such as, simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve Bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markova decision processes, or Deep Deterministic Policy Gradient (DDPG) machine learning algorithms to generate aliment instruction set 140, see FIG. 2 below for further details regarding machine learning models. Aliment machine learning model is trained by receiving training data from a second training set 152 correlating disorder state label 124 to aliment instruction set 140. Second training set 152 may include edibles of interest that may ameliorate or prevent the likelihood of an autoimmune disorder. For example, vitamin D has been shown to aid in preventing the autoimmune disorder diabetes and can be found in high quantities in the flesh of salmon, tuna, or mackerel. Additionally or alternatively, omega-3 fatty acids have been found to reduce the effects of inflammatory bowel disorder and can be found in high quantities in edibles such as mackerel, salmon, herring, oysters, chia seeds, walnuts, soybeans, and the like thereof.

Still referring to FIG. 1, computing device 104 may utilize an autoimmune machine learning process 156 to train autoimmune databank 120. Autoimmune machine learning process 156 may obtain physiological data associated with a marker from a third training set 160 and train autoimmune databank 120 as a function of the novel markers associated with autoimmune disorders. For example, a novel marker associated with Gaucher disease includes semaphorin 7A, autoimmune machine learning process 156 may obtain physiologic data from that marker and identify novel markers that are physiologically similar to semaphorin 7A to train autoimmune databank 120. Third training set 160 relates physiological data associated with markers to autoimmune databank 120, which aids in training autoimmune databank to determine novel markers that may indicate the likelihood for developing an autoimmune disorder or an active autoimmune disorder. Third training set 160 is discussed in further detail below. Autoimmune machine learning process 156 further aids in generating autoimmune databank 120 as a function of the identified autoimmune disorder and third training set 160.

With continued reference to FIG. 1, computing device 104 locates a plurality of provider aliment possibilities 168. A "provider aliment possibility," as used in this disclosure is an edible that is available from a provider such that the user may obtain the edible that correlates to the edible program generated by aliment instruction set 140. Computing device 104 may receive a plurality of alimentary provider possibilities from an alimentary provider device 164 of a plurality of alimentary provider devices 164*a-m*. An alimentary provider device 164 may transmit information to computing device 104 relating menu items and meal choices available from alimentary providers consisting of one or more edibles, for instance and without limitation in the form of a meal package, prepared meal, meal kit, or the like. Alimentary provider device 164 may include any device suitable for use as computing device 104, as described above, which may be operated by an alimentary provider. Provider alimentary possibilities may include, without limitation a "meal package," defined as an ingredient combination to be prepared by an end user; preparation may include heating and/or reheating a cooked meal, combining ingredients, chopping ingredients, marinating ingredients, heating ingredients, boiling ingredients, and/or any other process of transforming ingredients into a meal. A meal package may come with instructions for preparation. A meal kit may instruct that users add water or other elements that may be external to meal package and/or provided by user.

Further referring to FIG. 1, an "alimentary provider," as used in this disclosure, is a person or entity that prepares alimentary products such as meals, food items, and/or drinks, including without limitation a restaurant, a food production service, a food delivery service, or the like. Provider ingredients of provider ingredient possibilities may include one or more ingredients, where an "ingredient" is any ingredient in any alimentary product. In an embodiment, each alimentary provider device 164 may indicate a time period, such as a date range, during which each ingredient is available, a geographic region within which each ingredient is available, or the like; alternatively or additionally, each alimentary provider device 164 may solely indicate current availability of each ingredient and/or report only ingredients that are available from an alimentary provider associated with the alimentary provider device 164 at the time that transmission occurs. Computing device 104 may store received provider ingredients in a provider ingredient datastore 172. Provider ingredient datastore 172 may include any data structure for ordered storage and retrieval of data, which may be implemented as a hardware or software module. Provider ingredient datastore 172 may be implemented, without limitation, as a relational database, a key-value retrieval datastore such as a NOSQL database, or any other format or structure for use as a datastore that a person skilled in the art would recognize as suitable upon review of the entirety of this disclosure. Provider ingredient datastore 172 may include a plurality of data entries and/or records as described above. Data entries in provider ingredient datastore may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in provider ingredient datastore may reflect categories, cohorts, and/or populations of data consistently with this disclosure. Provider ingredient datastore 172 may be located in memory of computing device 104 and/or on another device in and/or in communication with system 100.

With continued reference to FIG. 1, computing device 104 may group provider ingredients within provider ingredient datastore 172 according to a geographical region in which the provider ingredients are available, which a user could enter information about using graphical user interface 112. Geolocation may indicate longitude and latitude where a user is located, GPS location, specified location, or the like thereof. Additionally or alternatively, computing device 104 may group provider ingredients within provider ingredient datastore 172 as a function of a time period during which the provider ingredients are available, and/or any other category that may be defined by data associated with any provider ingredient as described in this disclosure. Provider ingredients may be grouped in provider ingredient datastore 172 according to identifiers of alimentary provider device 164, and/or associated alimentary providers, that transmitted provider ingredients; in other words, computing device 104 and/or other devices in and/or communicating with system 100 may be able to query provider ingredient datastore 172 using an identifier of an alimentary provider and receive in return a list of ingredients currently available to that provider and/or that will be available to that alimentary provider within a given time period and/or at a particular location.

Further referring to FIG. 1, computing device 104 is configured to generate an arranged list 176 of alimentary possibilities by identifying a plurality of provider alimentary possibilities 168 as a function of the aliment instruction set 140. An "arranged list," as used in this disclosure, is an ordered collection of data elements for which an order of presentation is defined according to ascending or descending values of a quantitative or other textual field associated with each element in the ordered collection. Computing device 104 may accomplish this, without limitation, by locating provider aliment possibility 168 corresponding to each provider device 164 of the plurality of provider devices 164*a-m*. Arranged list 176 may be generated as a quantitative value such that the aliment provider possibility 168 may have an impact value that corresponds to the edibles provided. This impact value may be correlated to the aliment instruction set 140 such that the highest impact value associated with the aliment instruction set 140 is displayed first, followed by the second highest impact value associated with the aliment instruction set 140. Computing device 104 is configured to represent an arranged list on a display, whereby a display may include any display as described herein, including for example a graphical user interface.

With continued reference to FIG. 1, computing device 104 may be further configured to obtain an aliment sequence from arranged list 176 and generate the updated arranged list as a function of a user preference. For example, a user may select a preference of a pescatarian meal from arranged list 176 generated as a function of the provider aliment possibilities and the aliment instruction set. Computing system

104 may then then update arranged list 176 as a function of the user preference selection to represent only pescatarian alimentary provider possibilities as a function of the aliment instruction set. Additionally or alternatively, computing system 104 may generate an updated arranged list 176 by determining an updated aliment instruction set 140 and generating updated arranged list 176 as a function of updated aliment instruction set 140. For example, an aliment instruction set may initially find chitinase 3-like 1 (cartilage glycoprotein-39) (CH13L1), which is a predisposition to develop rheumatoid arthritis, and then subsequently find YKL-40 which is marker associated with the active autoimmune disorder rheumatoid arthritis. The updated marker 116 may then alter the disorder state label 124 from a likelihood for an autoimmune disorder to an active autoimmune disorder, which may update the aliment instruction set 140 from an aliment predisposition instruction set to a symptoms aliment instruction set. Computing system 104 may then generate updated arranged list 176 as a function of updated aliment instruction set 140 and provider aliment possibilities 168 to provide an edible program containing more beta-cryptoxanthin, which has been found to alleviate symptoms associated with rheumatoid arthritis.

In an embodiment, and further referring to FIG. 1, computing device 104 may be configured to represent arranged list 176 and/or at least recommended edible program 180 to the user. Representing may include displaying arranged list 176 on graphical user interface. Computing device 104 may receive a user selection of an ingredient combination, for instance by way of user selection of a link, button and/or other display element corresponding to a recommended edible program 180. Computing device 104 may automatically initiate preparation and/or delivery of selected ingredient combination, for instance and without limitation by transmitting indication of selection to a corresponding alimentary provider device 164.

Still referring to FIG. 1, in an embodiment, steps described above may be performed iteratively; at each iteration user may select one or more alimentary possibilities, upon which computing device 104 may regenerate arrangements, represent regenerated arrangements, generate recommended edible program 176, and/or represent recommended alimentary possibilities 176. Iteration may be repeated until an autoimmune disorder as described above has been suppressed or treated with user selections. Recommended alimentary possibilities 176 may be represented concurrently with arranged list 172, for instance and without limitation in separate windows, frames, or the like, permitting user to select recommended edible program 176, ingredient possibilities from arranged list 172, or the like thereof. Upon presentation with a recommended edible program 176, user may accept entire recommended edible program, accept a subset thereof while rejecting a remainder thereof, accept one or more while selecting another alimentary from arranged list 172, or rejecting all recommended alimentary possibilities 176 and selecting one or more other edible plans from arranged list 172.

Figure 2:
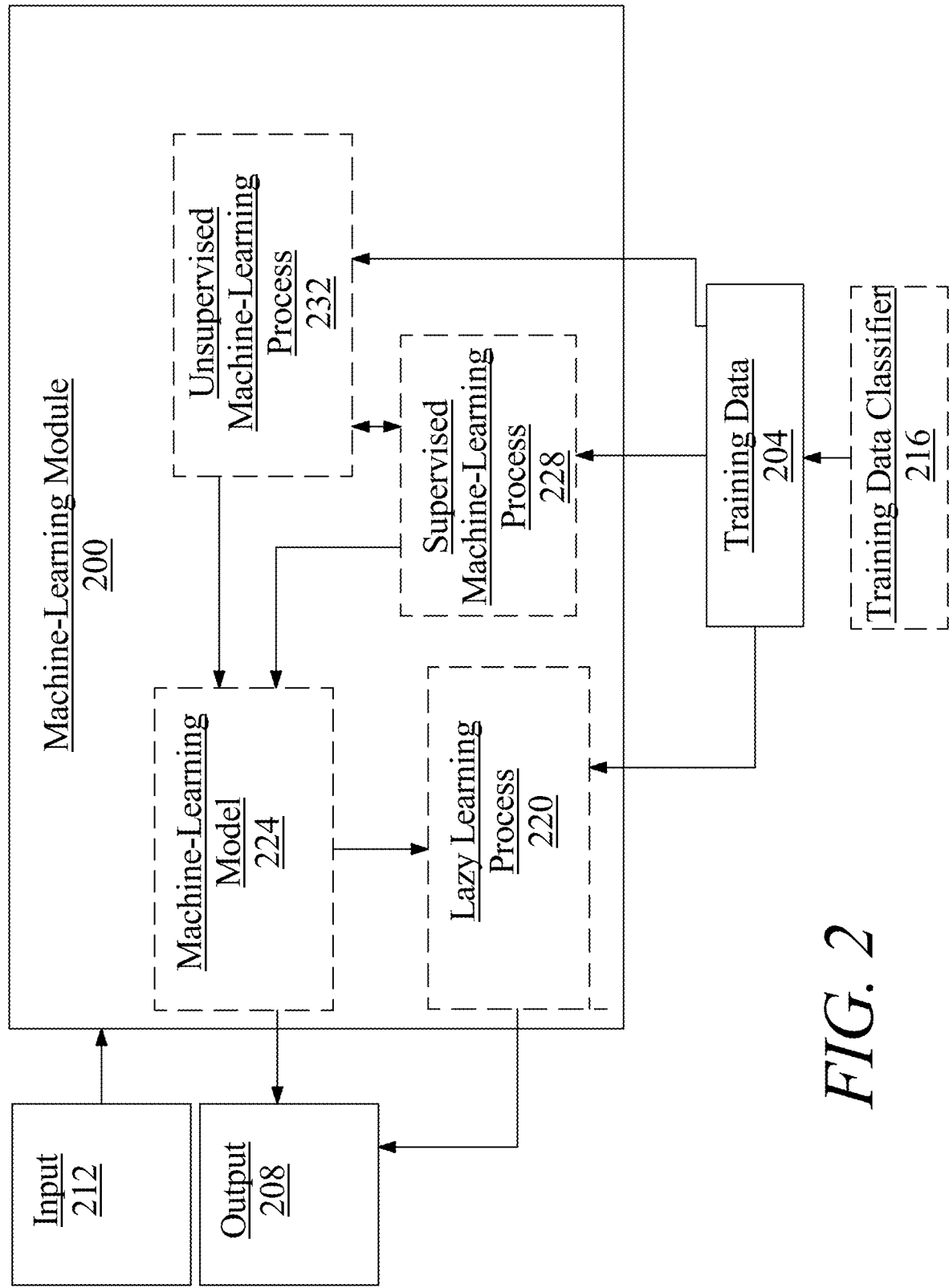
FIG. 2 is a block diagram of an exemplary embodiment of a machine-learning module.

Referring now to FIG. 2, an exemplary embodiment of a machine-learning module 200 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 204 to generate an algorithm that will be performed by a computing device/module to produce outputs 208 given data provided as inputs 212; this is in contrast to a non-machine learning software program where the commands to be executed are determined in advance by a user and written in a programming language.

Still referring to FIG. 2, "training data," as used herein, is data containing correlations that a machine-learning process may use to model relationships between two or more categories of data elements. For instance, and without limitation, training data 204 may include first training set, second training set, third training set, among a plurality of other data entries, each entry representing a set of data elements that were recorded, received, and/or generated together; data elements may be correlated by shared existence in a given data entry, by proximity in a given data entry, or the like. Multiple data entries in training data 204 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 204 according to various correlations; correlations may indicate causative and/or predictive links between categories of data elements, which may be modeled as relationships such as mathematical relationships by machine-learning processes as described in further detail below. Training data 204 may be formatted and/or organized by categories of data elements, for instance by associating data elements with one or more descriptors corresponding to categories of data elements. As a non-limiting example, training data 204 may include data entered in standardized forms by persons or processes, such that entry of a given data element in a given field in a form may be mapped to one or more descriptors of categories. Elements in training data 204 may be linked to descriptors of categories by tags, tokens, or other data elements; for instance, and without limitation, training data 204 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 2, training data 204 may include one or more elements that are not categorized; that is, training data 204 may not be formatted or contain descriptors for some elements of data. Machine-learning algorithms and/or other processes may sort training data 204 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns updated by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatically may enable the same training data 204 to be made applicable for two or more distinct machine-learning algorithms as described in further detail below. Training data 204 used by machine-learning module 200 may correlate any input data as described in this disclosure to any output data as described in this disclosure. As a non-limiting illustrative example, a first training set m input to marker machine learning model to output the marker classifier.

Further referring to FIG. 2, training data may be filtered, sorted, and/or selected using one or more supervised and/or unsupervised machine-learning processes and/or models as described in further detail below; such models may include without limitation a training data classifier 216. Training data classifier 216 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 200 may generate a classifier using a classification algorithm, defined as a processes whereby a computing device and/or any module and/or component operating thereon derives a classifier from training data 204. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 216 may classify elements of training data to specific autoimmune disorders, or autoimmune disorder types, where an autoimmune disorder type may be classified based on the location of the autoimmune disorder in the body.

Still referring to FIG. 2, machine-learning module 200 may be configured to perform a lazy-learning process 220 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 204. Heuristic may include selecting some number of highest-ranking associations and/or training data 204 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 2, machine-learning processes as described in this disclosure may be used to generate machine-learning models 224. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 224 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 224 may be generated by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 2, machine-learning algorithms may include at least a supervised machine-learning process 228. At least a supervised machine-learning process 228, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include first training set as described above as inputs, marker classifier as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 204. Persons skilled in the art, upon reviewing the entirety of this disclosure, will be aware of various possible variations of at least a supervised machine-learning process 228 that may be used to determine relation between inputs and outputs. Supervised machine-learning processes may include classification algorithms as defined above.

Further referring to FIG. 2, machine learning processes may include at least an unsupervised machine-learning processes 232. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 2, machine-learning module 200 may be designed and configured to create a machine-learning model 224 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be updated to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 2, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 2, models may be generated using alternative or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using training data 204.

Figure 3:
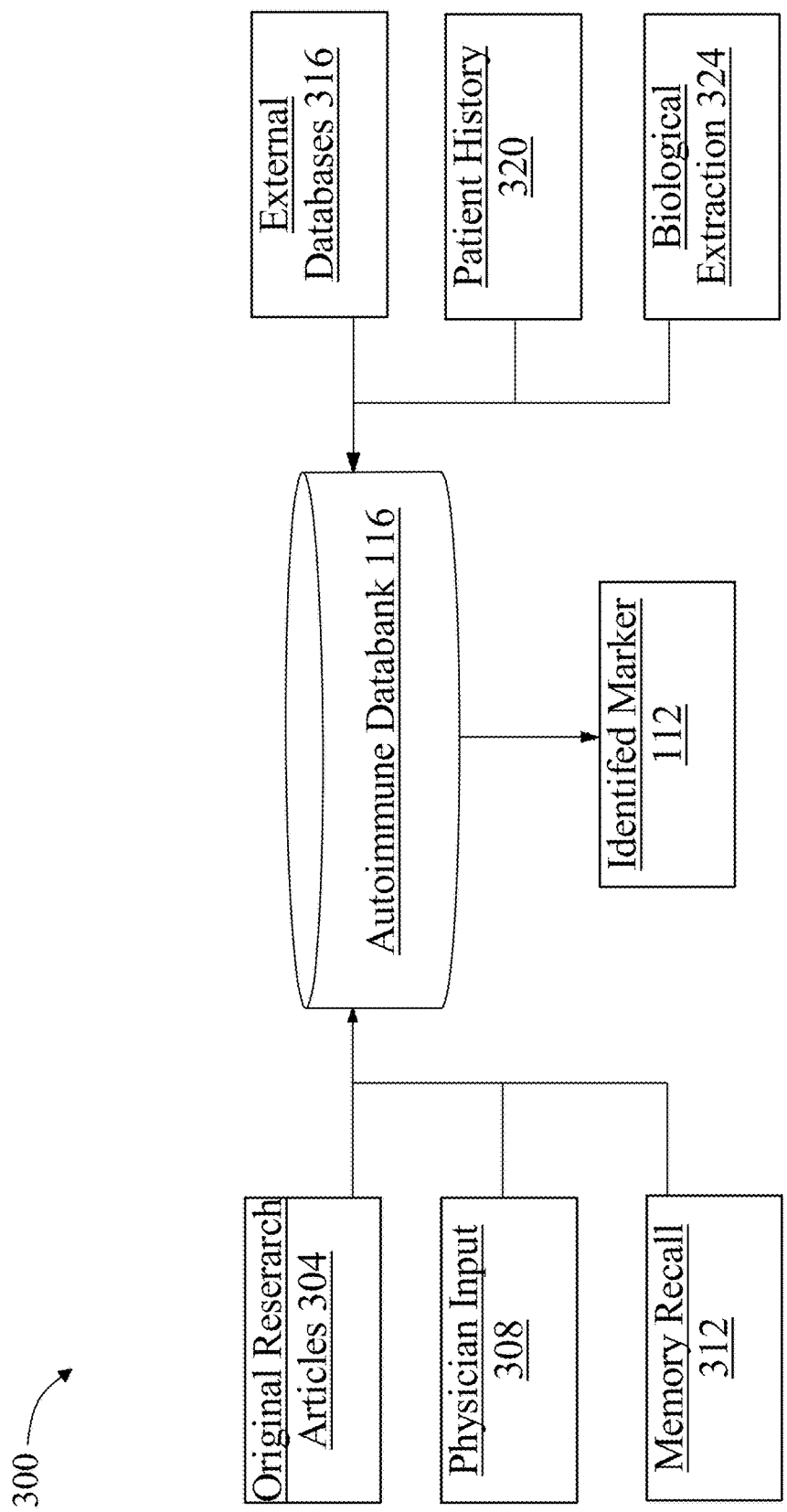
FIG. 3 is a block diagram illustrating the autoimmune database according to an embodiment of the invention.

Referring now to FIG. 3, an exemplary embodiment 300 of autoimmune databank 120 is illustrated. An autoimmune databank 120 may include data collected from one or more inputs, containing information and/or expert inputs relating to autoimmune disorders, markers, disorder state labels and the like. Inputs may be received by computing device 104 utilizing any network methodology as described herein. In an embodiment, an input may include an input from an original research article 304. Original research articles 304 may allow for novel markers that are recently published to be inputted and stored in autoimmune database 120. Original research articles may include, without limitation, articles from reputable journals such as science, nature, and the like thereof, peer reviewed studies, RCT studies, and the like thereof. Autoimmune database 120 may include input from a physician input 308. As used in this disclosure "physician input" may be defined as expert input from medical professionals such as medical doctors, nurse practitioners, Ph.D. researchers, physician assistants, and the like thereof. These medical professionals may be considered an expert because they have board certifications in certain areas, they have clinical trial experience, they publish textbooks or peer reviewed medical media on autoimmune disorder topics, they give presentations at medical conferences, they have a practice relating to autoimmune disorders, they are involved in a committee that pertains to autoimmune disorders, or the like thereof. Physician input 308 may be markers including, but not limited to, markers identified upon a user examination. Autoimmune database 120 may include input from a memory recall 312. This may include, without limitation, previous markers identified associated with an autoimmune database, previous markers identified that are not associated with an autoimmune disorder, other markers that have been identified relating to a user. An external database 316 may be used as an input to generate autoimmune database 120. External database 316 include, but are not limited to, databases such as NIST as produced by the U.S. department of commerce of Washington, D.C., ProteinProspector produced by the Regents of the University of California of Oakland, Calif., GoBIOM as produced by Excelra of Cambridge, Mass., or the like thereof. Autoimmune database 120 may include inputs from a patient history 320. Patient history 320 may include one or more elements of demographic information relating to the user. This may include, without limitation, medical history, ethnicity, national origin, age, language, sex, geographic location of residence, or the like thereof. A biological extraction 324 may be included as an input to autoimmune database 120.

Figure 4:
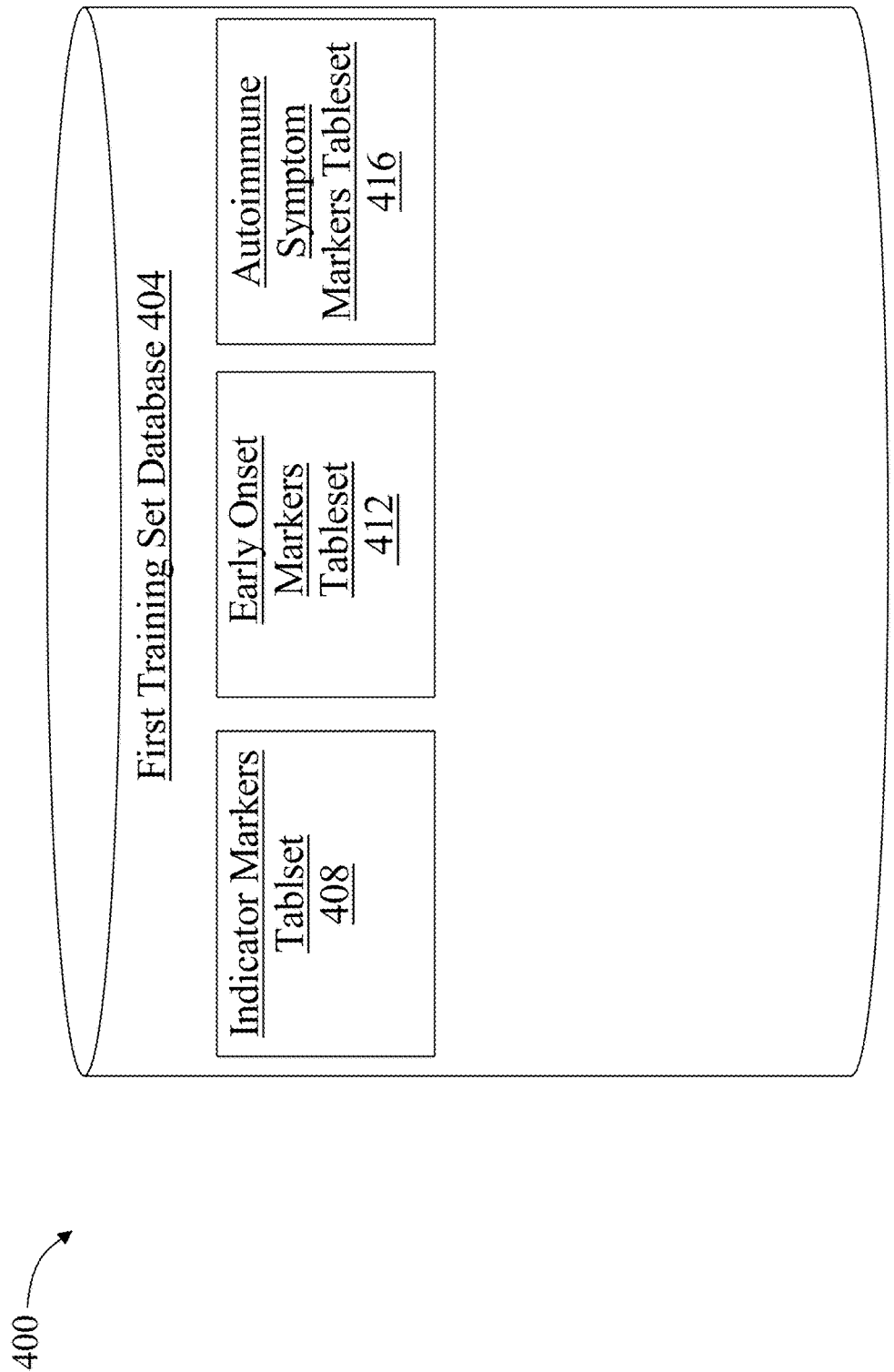
FIG. 4 is a block diagram of a first training set database according to an embodiment of the invention.

Referring now to FIG. 4, an exemplary embodiment 400 of first training set database 404 is illustrated. First training set database 404 may include an indicators marker set 408, which may indicate the likelihood of developing an autoimmune disorder. This may include, without limitation, markers such as proteins, cells, vitamins, electrolytes, or chemicals present in a user that indicate a predisposition for developing autoimmune disorder in the future. First training set database 404 may include an early onset marker set 412, which may indicate the progression of autoimmune disorder. For example, early onset marker set 412 may include, but is not limited to, HLA-DRB1, Anti-CCP antibodies, or HLA-DR4 for the early onset identification of rheumatoid arthritis. First training set database 404 may include an autoimmune symptom marker set 416 which may indicate an active autoimmune disorder that is presenting symptoms in a user. For instance, autoimmune symptom marker set 416 may include markers such as, without limitation, interleukin-6, tumor necrosis factor receptor type I, vascular cell adhesion molecule 1, epidermal growth factor, vascular endothelial growth factor A, YKL-40, matrix metalloproteinase 1, matrix metalloproteinase 3, C-reactive protein, serum amyloid A, Leptin, or resistin for rheumatoid arthritis.

Figure 5:
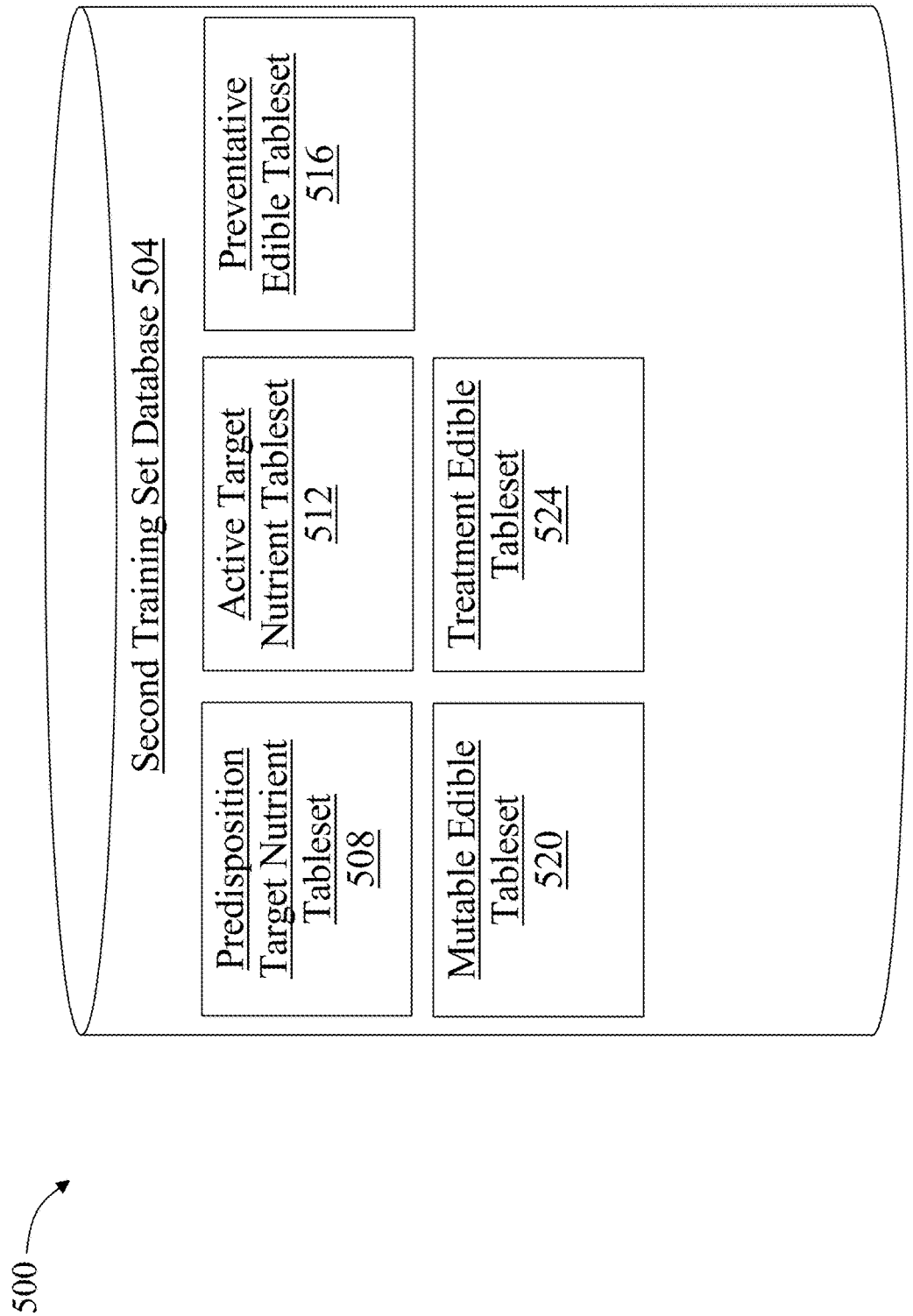
FIG. 5 is a block diagram of a second training set database according to an embodiment of the invention.

Referring now to FIG. 5, an exemplary embodiment 500 of second training set database 504 is illustrated. Second training set database 504 may include a predisposition target nutrient table set 508, which may include a target nutrient or a plurality of target nutrients for a user to consume as a preventative method towards autoimmune disorder. This may include, without limitation, vitamins, electrolytes, proteins, carbohydrates, fats, or minerals that may aid in as a preventative method towards autoimmune disorder. Second training set database 504 may include an active target nutrient table set 512, which may include a target nutrient or a plurality of target nutrients for a user to consume as a treatment method towards autoimmune disorder. This may include, without limitation, vitamins, electrolytes, proteins, carbohydrates, fats, or minerals that may aid in as a treatment method towards autoimmune disorder. Second training set database 504 may include a preventative edible table set 516, which may consist of edibles that contain the target nutrients associated with predisposition target nutrient table set 508. Second training set database 504 may include a mutable edible table set 520, which may consist of edibles that contain the target nutrients associated with active target nutrient table set 512. This may include target nutrients that allow for a reversible edible program towards autoimmune disorder, such that the autoimmune disorder may be ameliorated from a user. Second training set database 504 may include a treatment edible table set 524, which may consist of edibles that contain the target nutrients associated with active target nutrient table set 512. Treatment edible table set 524 may include, without limitation, edibles that contain target nutrients such that symptoms associated with autoimmune disorder may be resolved in a user.

Figure 6:
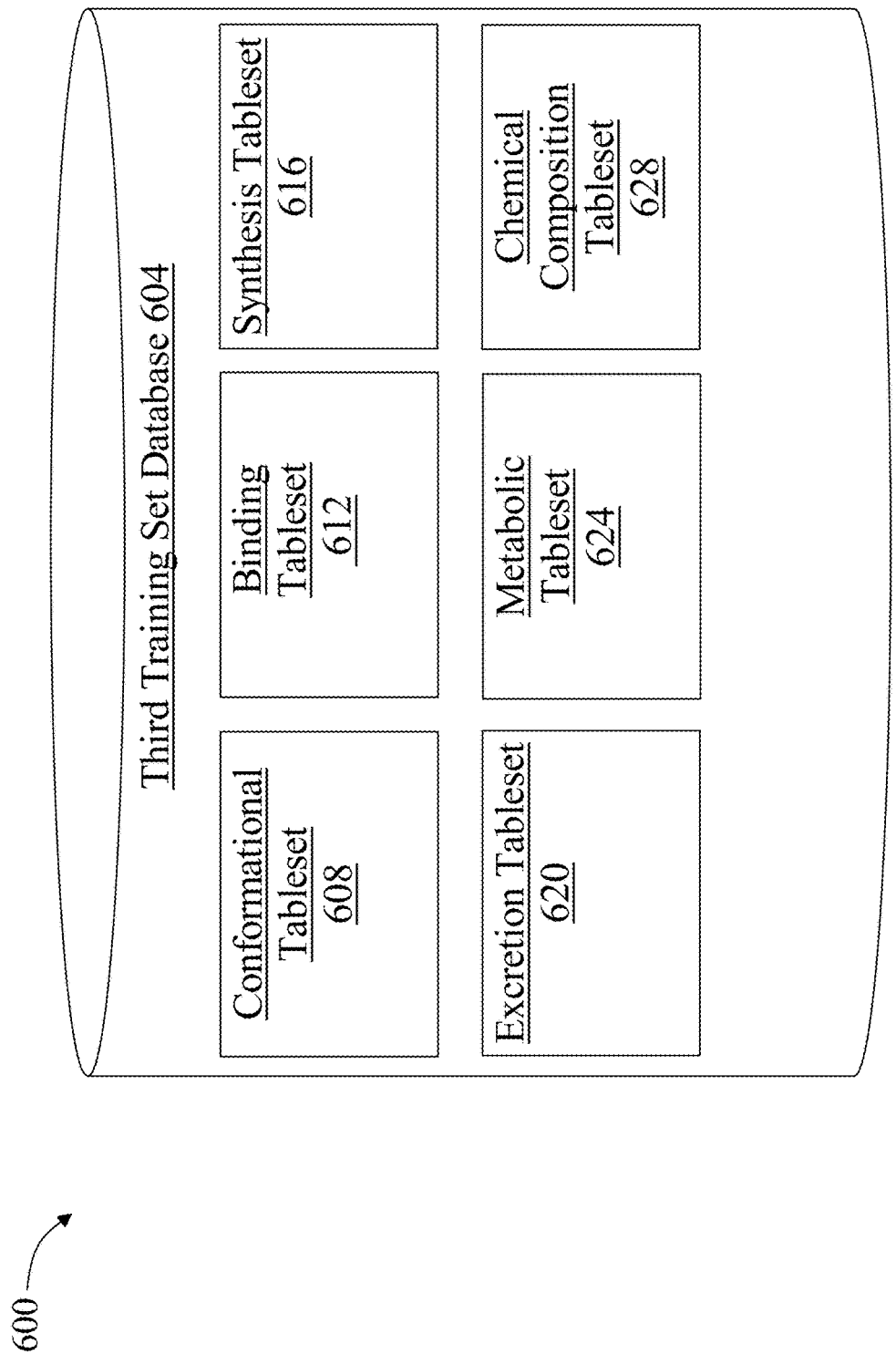
FIG. 6 is a block diagram of a third training set database according to an embodiment of the invention.

Referring now to FIG. 6, an exemplary embodiment 600 of second training set database 604 is illustrated. Third training set database 604 may include a conformational table set 608, indicating the spatial arrangement of marker 116. This may include, without limitation bond connectivity, stereoisomerism, and spatiotemporal characteristics of marker 116. Third training set database 604 may include a binding table set 612, which may include binding properties of marker 116. Binding properties may include, but are not limited to, van Der Waals forces, π-πbonding, dipole-dipole binding, ionic binding, and metallic binding. Binding table set 612 may include binding properties associated with marker 116 as a function of the induced fit binding in a user. Third training set database 604 may include a synthesis tablet 616, which may indicate the synthetic route of marker 116 as a function of autoimmune disorder. This may indicate the progression, location, and type of user autoimmune disorder. Third training set database 604 may include an excretion table set 620. Excretion table set 620 may include one or more elements of marker 116 elimination from a user. Marker 116 elimination may be utilized to track and monitor the progress of autoimmune disorder. Third training set database 604 may include a metabolic table set 624 associated with marker 116, which may indicate to computing system 104 other markers associated with autoimmune disorder to identify. For example, a user may have diabetes and present a marker of glucose, which is metabolized to glucose-6-phosphate. Metabolic table set 624 may allow computing system 104 to identify additional metabolites associated with marker 116, or in this instance glucose. Third training set database 604 may include a chemical composition table set 628, which may indicate the chemical or biological composition of marker 116. The chemical or biological composition of marker 116 may allow computing system 104 to select an edible program that may interact with marker 116.

Figure 7:
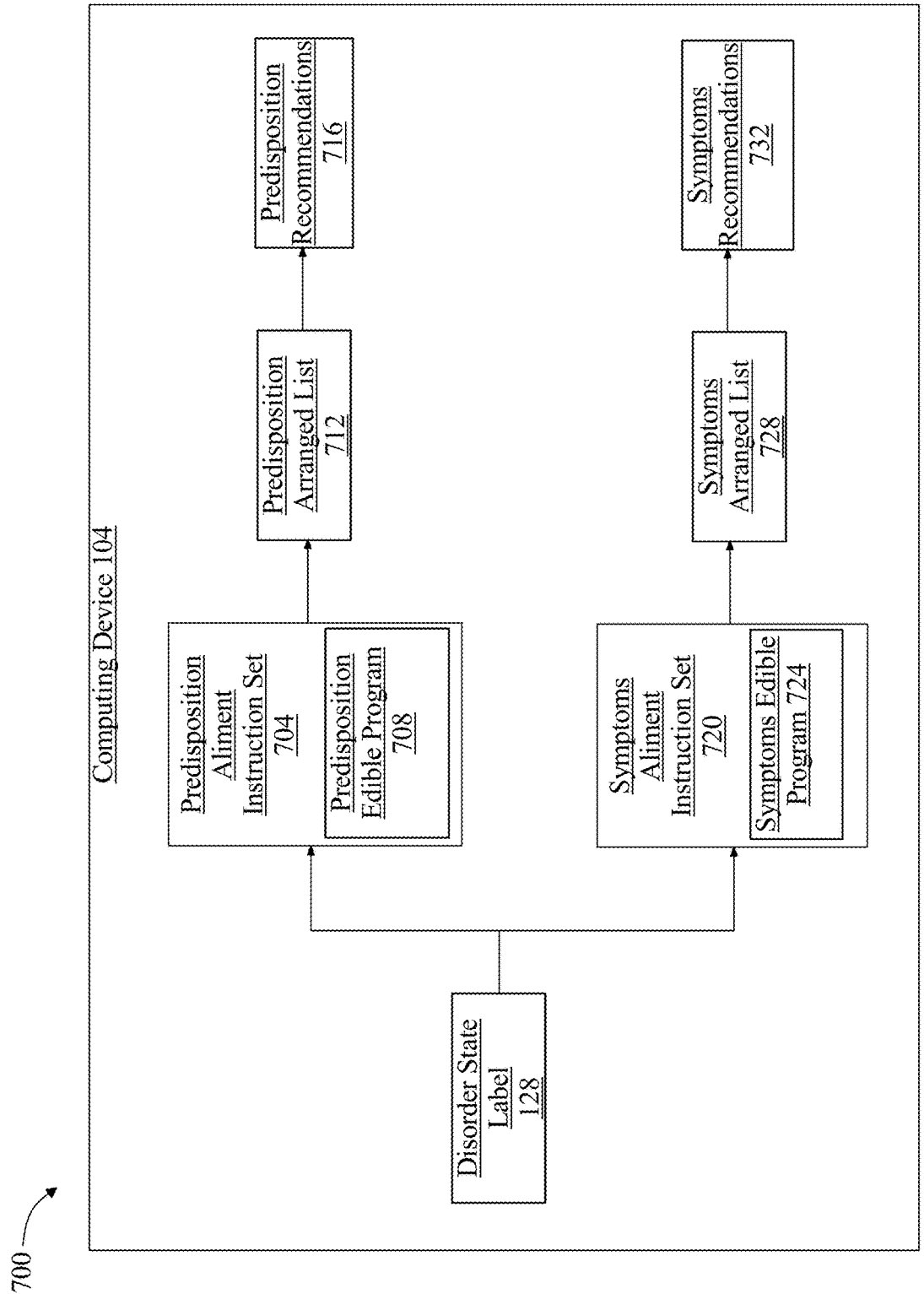
FIG. 7 is a representative diagram illustrating recommendation selection according to an embodiment of the present invention.

Referring now to FIG. 7, an exemplary embodiment 700 recommendation selection is illustrated. Computing device 104 may be configured to generate various edible recommendations 180 as a function of disorder state label 124. Disorder state label 124 may denote a likelihood of developing autoimmune disorder, which may indicate aliment instruction set to modify to a predisposition aliment instruction set 704. Predisposition aliment instruction set 704 may include a predisposition edible program in the preventative measure of autoimmune disorder. Predisposition aliment instruction set 704 may generate a predisposition arranged list 712, which may arrange provider alimentary possibilities as a function of the predisposition aliment instruction set 704. Predisposition arranged list 712, may then generate a predisposition recommendation 716 to user as a function of the predisposition arranged list 712. Disorder state label 124 may denote a user may have symptoms of autoimmune disorder, which may indicate aliment instruction set 140 to generate a symptoms aliment instruction set 720. Symptoms aliment instruction set 720 may include an edible program for the treatment of an autoimmune disorder. Symptoms aliment instruction set 720 may generate a symptom arranged list 728, which may arrange provider alimentary possibilities as a function of the symptoms aliment instruction set 720. Symptoms arranged list 728, may then generate a symptoms recommendation 732 to user.

Figure 8:
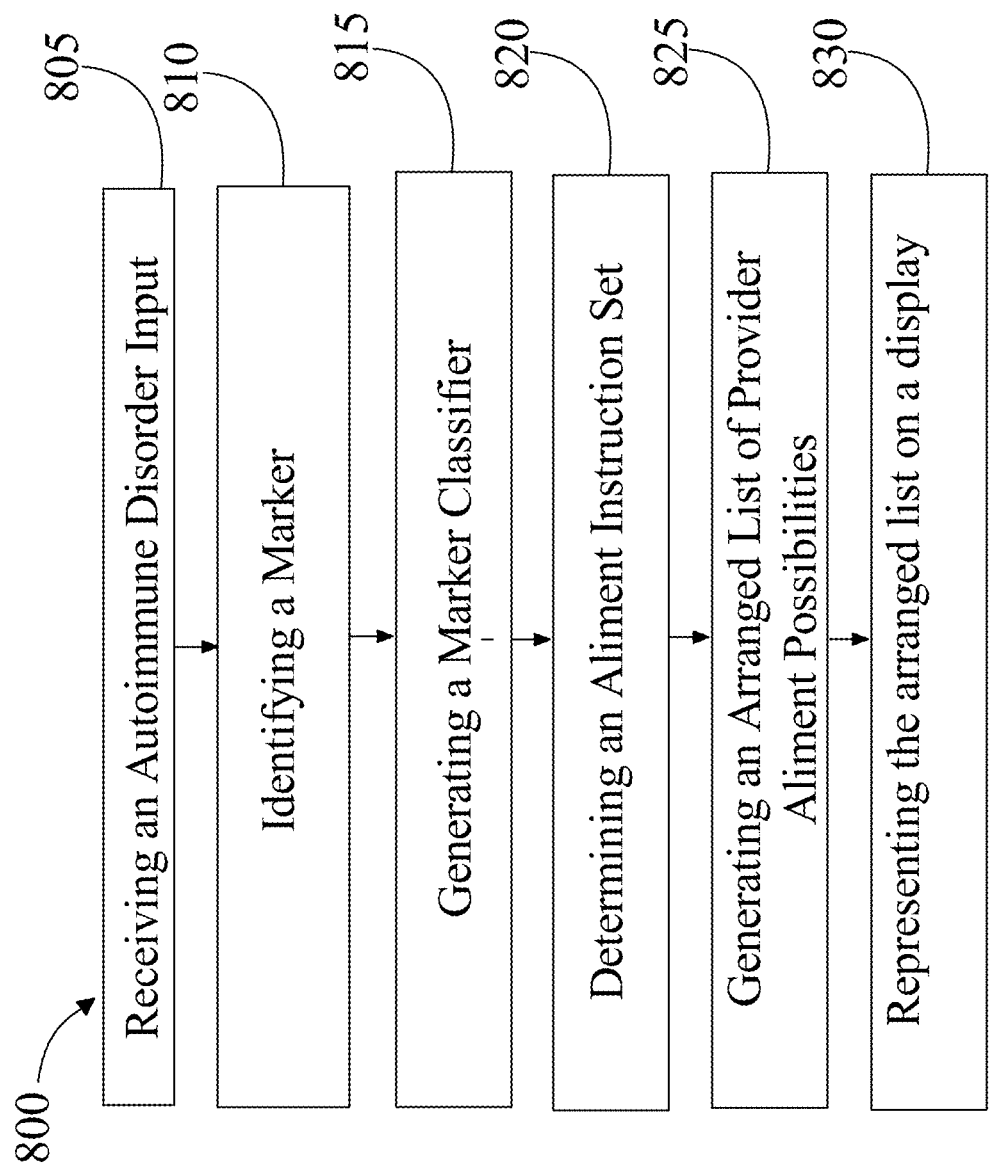
FIG. 8 is a process flow diagram illustrating an exemplary method of representing an arranged list of provider aliment possibilities.

Referring now to FIG. 8, an exemplary embodiment of a method 800 of arranging provider alimentary possibilities is illustrated. At step 805, computing device 104 receives a user autoimmune disorder input 108 including a plurality of user autoimmune disorders. Receiving user autoimmune disorder input may comprise representing a plurality of autoimmune disorders on graphical user interface 112 and receiving a user input relating to the plurality of autoimmune disorders. For example, a user may be presented with a list of the top twenty most prevalent autoimmune disorders. The user may select one or more of these autoimmune disorder inputs. Additionally or alternatively, receiving the autoimmune disorder may be a function of a marker. For example, the celiac disorder may be received as a function of Interleukin 15; this may be implemented, without limitation, as described above in reference to FIGS. 1-7.

With continued reference to FIG. 8, at step 810, computing device 104 identifies a marker 116 as a function of the autoimmune disorder within an autoimmune databank 120; this may be implemented, without limitation, as described above in reference to FIGS. 1-7. Identifying marker 116 may include obtaining physiological data associated with marker 116. For example, physiological data may be from one or more inputs, containing information and/or expert inputs relating to autoimmune disorders, markers, disorder state labels and the like. Identifying marker 116 may then include generating an autoimmune machine learning process 156 as a function of a third training set 160 and generating autoimmune databank 120 as a function of the generated autoimmune machine learning process 156, for instance as described above. For example, if a marker albumin is found users that are all experiencing rheumatoid arthritis, the autoimmune machine learning process will integrate the training data with that biomarker to enhance autoimmune databank.

With continued reference to FIG. 8, at step 815, computing device 104 generates a marker classifier 128 as a function of first training set 136, such that disorder state label 124 may be outputted. The first training set relates marker 120 to disorder state label 124. Disorder state label 124 may specify an active autoimmune disorder or a likelihood for an autoimmune disorder. This may be implemented, without limitation, as described above in reference to FIGS. 1-7.

With continued reference to FIG. 8, at step 820, computing device 104 determines an aliment instruction set 140 as a function of edible programs 144; this may be implemented, without limitation, as described above in reference to FIGS. 1-7. Determining aliment instruction set 140 may include, obtaining a second training set 152 and determining the aliment instruction set 140 as a function of the second training set 152 as a function of the aliment machine-learning process 148 for instance as described above. Edible program 144 may be further comprised of a mutable edible program and a treatment edible program as stated above. Computing device 104 receives from each alimentary provider device 164 of a plurality of alimentary provider device 164a-m, a plurality of provider aliment possibilities 168.

With continued reference to FIG. 8, at step 825 computing device 104 generates arranged list 176 of alimentary possibilities as a function of the plurality of provider aliment possibilities 168; this may be implemented, without limitation, as described above in reference to FIGS. 1-7. Generating the arranged list 176 of alimentary possibilities may include identifying a plurality of provider alimentary possibilities as a function of the plurality edible programs and generating arranged list 176 as a function of the plurality of provider alimentary possibilities. Identifying the plurality of provider alimentary possibilities may include comparing, for each provider edible plan of the plurality of provider alimentary possibilities 168, an impact value corresponding to the provider ingredient possibilities, and eliminating each provider ingredient combination that fails the threshold comparison. Identifying the plurality of provider alimentary possibilities may include receiving at least a user parameter and identifying the plurality of provider alimentary possibilities to match the at least a user parameter.

With continued reference to FIG. 8, at step 830, computing device 104 represents an arranged list of provider aliment possibilities on a display; wherein this may be implemented, without limitation, as described above in reference to FIGS. 1-7. Computing device 104 obtains a user preference of provider aliment possibilities 168 from the represented list of provider aliment possibilities corresponding to an edible of the plurality of autoimmune disorder target nutrients. Obtaining user preference may include representing arranged list 176 on a user client device and receiving a user preference of the represented arranged list 176. Computing device 104 generates updated arranged list 176 of alimentary possibilities as a function of user preference and aliment instruction set 140. Generating updated arranged list 176 may include obtaining an aliment sequence from the arranged list and generating an updated arranged list as a function of a user preference. For example, a user may select a preference of a pescatarian meal, which may then update the arranged list as a function of the user preference selection. Additionally or alternatively, generating an updated arranged list may include determining an updated aliment instruction set and generating the updated arranged list as a function of the updated aliment instruction set. For example, an aliment instruction set may be updated from a predisposition aliment instruction set to a symptoms aliment instruction set, which may then generate an updated arranged list as a function of the altered aliment instruction set.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any possibilities thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any possibilities thereof. In one example, a computing device may include and/or be included in a kiosk.

Figure 9:
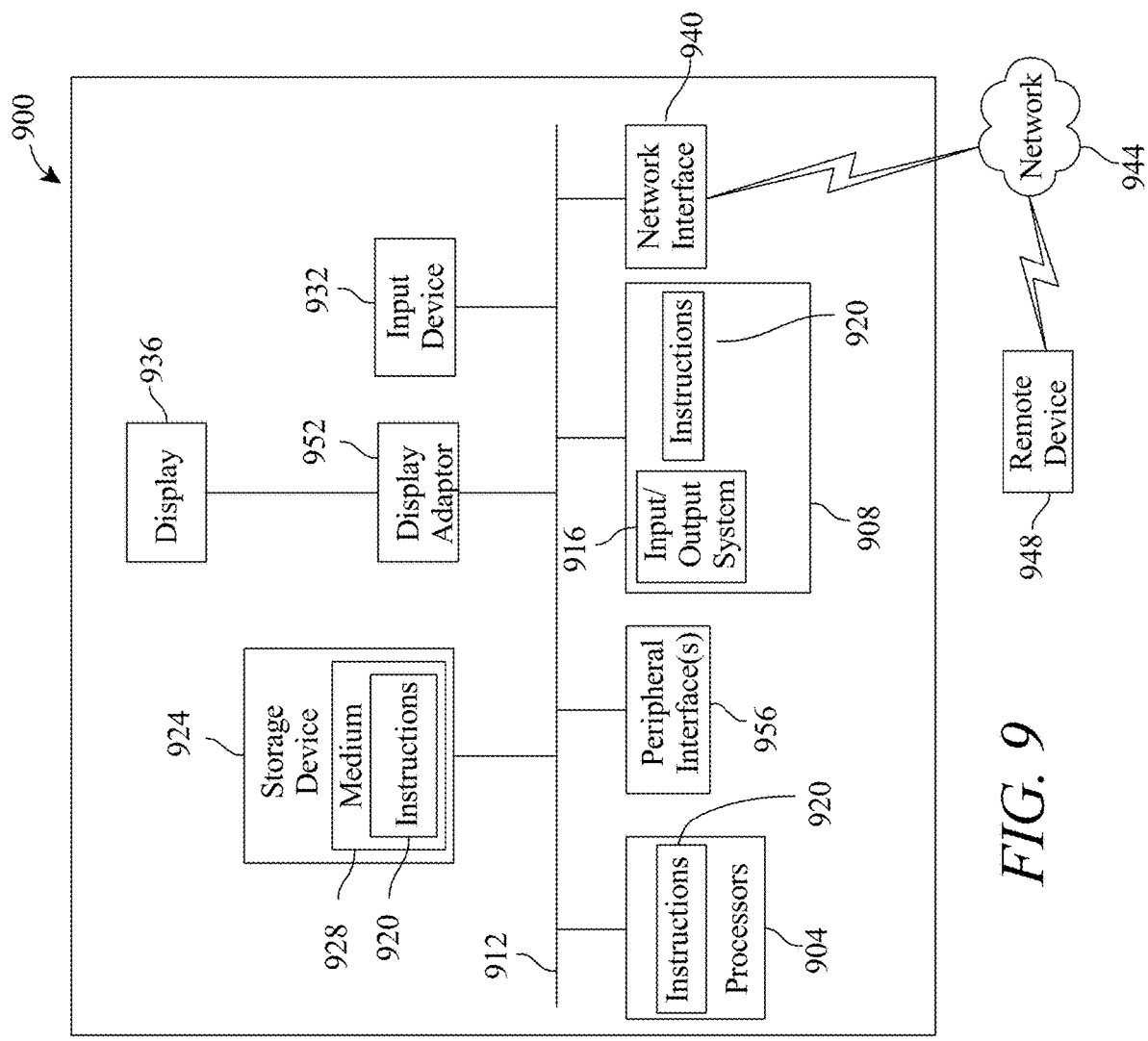
FIG. 9 is a block diagram of a computing system that can be used to implement any one or more of the methodologies disclosed herein and any one or more portions thereof.

FIG. 9 shows a diagrammatic representation of one embodiment of computing device 104 in the exemplary form of a computer system 900 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 900 includes a processor 904 and a memory 908 that communicate with each other, and with other components, via a bus 912. Bus 912 may include any of several types of bus structures including, but not limited to, a memory bus, a memory controller, a peripheral bus, a local bus, and any possibilities thereof, using any of a variety of bus architectures.

Processor 904 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 904 may be organized according to Von Neumann and/or Harvard architecture as a non-limiting example. Processor 904 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC)

Memory 908 may include various components (e.g., machine-readable media) including, but not limited to, a random-access memory component, a read only component, and any possibilities thereof. In one example, a basic input/output system 916 (BIOS), including basic routines that help to transfer information between elements within computer system 900, such as during start-up, may be stored in memory 908. Memory 908 may also include (e.g., stored on one or more machine-readable media) instructions (e.g., software) 920 embodying any one or more of the aspects and/or methodologies of the present disclosure. In another example, memory 908 may further include any number of program modules including, but not limited to, an operating system, one or more application programs, other program modules, program data, and any possibilities thereof.

Computer system 900 may also include a storage device 924. Examples of a storage device (e.g., storage device 924) include, but are not limited to, a hard disk drive, a magnetic disk drive, an optical disc drive in combination with an optical medium, a solid-state memory device, and any possibilities thereof. Storage device 924 may be connected to bus 912 by an appropriate interface (not shown). Example interfaces include, but are not limited to, SCSI, advanced technology attachment (ATA), serial ATA, universal serial bus (USB), IEEE 1394 (FIREWIRE), and any possibilities thereof. In one example, storage device 924 (or one or more components thereof) may be removably interfaced with computer system 900 (e.g., via an external port connector (not shown)). Particularly, storage device 924 and an associated machine-readable medium 928 may provide nonvolatile and/or volatile storage of machine-readable instructions, data structures, program modules, and/or other data for computer system 900. In one example, software 920 may reside, completely or partially, within machine-readable medium 928. In another example, software 920 may reside, completely or partially, within processor 904.

Computer system 900 may also include an input device 932. In one example, a user of computer system 900 may enter commands and/or other information into computer system 900 via input device 932. Examples of an input device 932 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any possibilities thereof. Input device 932 may be interfaced to bus 912 via any of a variety of interfaces (not shown) including, but not limited to, a serial interface, a parallel interface, a game port, a USB interface, a FIREWIRE interface, a direct interface to bus 912, and any possibilities thereof. Input device 932 may include a touch screen interface that may be a part of or separate from display 936, discussed further below. Input device 932 may be utilized as a user selection device for selecting one or more graphical representations in a graphical interface as described above.

A user may also input commands and/or other information to computer system 900 via storage device 924 (e.g., a removable disk drive, a flash drive, etc.) and/or network interface device 940. A network interface device, such as network interface device 940, may be utilized for connecting computer system 900 to one or more of a variety of networks, such as network 944, and one or more remote devices 948 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing device 104s, and any possibilities thereof. A network, such as network 944, may employ a wired and/or a wireless mode of communication. In general, any network topology may be used. Information (e.g., data, software 920, etc.) may be communicated to and/or from computer system 900 via network interface device 940.

Computer system 900 may further include a video display adapter 952 for communicating a displayable image to a display device, such as display device 936. Examples of a display device include, but are not limited to, a liquid crystal display (LCD), a cathode ray tube (CRT), a plasma display, a light emitting diode (LED) display, and any possibilities thereof. Display adapter 952 and display device 936 may be utilized in combination with processor 904 to provide graphical representations of aspects of the present disclosure. In addition to a display device, computer system 900 may include one or more other peripheral output devices including, but not limited to, an audio speaker, a printer, and any possibilities thereof. Such peripheral output devices may be connected to bus 912 via a peripheral interface 956. Examples of a peripheral interface include, but are not limited to, a serial port, a USB connection, a FIREWIRE connection, a parallel connection, and any possibilities thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature possibilities in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for representing an arranged list of provider aliment possibilities, the system comprising:
   a computing device, the computing device designed and configured to:
   receive an input representing an autoimmune disorder;
   identify a marker of the user, wherein identifying the marker of the user comprises:
      comparing the represented autoimmune disorder to a list of autoimmune disorders stored with an autoimmune data bank, wherein each autoimmune disorder in the list of autoimmune disorders is associated with a respective marker; and
      identifying the marker of the user as a function of the comparison of the represented autoimmune disorder to the list of autoimmune disorders;
   generate a marker classifier, wherein generating the marker classifier comprises:
      training the marker classifier according to a first training set correlating each of a plurality of markers to a respective disorder state label such that the trained marker classifier is configured to receive the identified marker of the user as an input and output a disorder state label as a function of the identified marker of the user and correlations of each of the plurality of marker to a respective disorder state label in the first training data;
   determine, as a function of the disorder state label, an aliment instruction set containing an edible program, wherein determining further comprises:
      generating an aliment machine-learning model, wherein generating the aliment machine-learning model comprises:
         training the aliment machine-learning model according to a second training set correlating each of a plurality of disorder state labels to a respective aliment instruction set such that the trained aliment machine-learning model is configured to receive the disorder state label as an input and output the edible program as a function of the disorder state label and correlations of each of the plurality of disorder state labels to a respective aliment instruction set in the second training data;
      assigning a respective impact score for each provider alimentary possibility of a plurality of provider alimentary possibilities; and
   generating an arranged list of provider aliment possibilities from a plurality of aliment possibilities as a function of the aliment instruction set and each respective impact score for each respective provider alimentary possibility of the plurality of provider alimentary possibilities; and
   represent the arranged list on a display.

2. The system of claim 1, wherein the computing device is further configured to:
   represent a plurality of autoimmune disorders; and
   receive a user input relating to the plurality of autoimmune disorders.

3. The system of claim 1, wherein the computing device is further configured to receive the autoimmune disorder as a function of the marker.

4. The system of claim 1, wherein the computing device is further configured to:
   obtain physiological data associated with the marker;
   generate an autoimmune machine-learning process using a third training set, the third training set relating physiological data associated with markers to an autoimmune databank; and
   generate an autoimmune databank as a function of the autoimmune machine-learning process.

5. The system of claim 1 wherein the disorder state label specifies an active autoimmune disorder.

6. The system of claim 1 wherein the disorder state label specifies a likelihood for an autoimmune disorder.

7. The system of claim 1, wherein the edible program further comprises a mutable edible program.

8. The system of claim 1, wherein the edible program further comprises a treatment edible program.

9. The system of claim 1, wherein the computing device is further configured to:
   obtain an aliment sequence from the arranged list; and
   generate an updated arranged list as a function of a user preference.

10. The system of claim 9 further comprising:
    determine an updated aliment instruction set; and
    generate the updated arranged list as a function of the updated aliment instruction set.

11. A method for representing an arranged list of provider aliment possibilities, the method comprising:
    receiving, by a computing device, an input representing an autoimmune disorder;
    identifying, by the computing device, a marker of the user, wherein identifying the marker of the user comprises:
       comparing the represented autoimmune disorder to a list of autoimmune disorders stored with an autoimmune data bank, wherein each autoimmune disorder in the list of autoimmune disorders is associated with a respective marker; and
       identifying the marker of the user as a function of the comparison of the represented autoimmune disorder to the list of autoimmune disorders;
    generating, by the computing device, a marker classifier, wherein generating the marker classifier comprises:
       training the marker classifier according to a first training set correlating each of a plurality of markers to a respective disorder state label such that the trained marker classifier is configured to receive the identified marker of the user as an input and output a disorder state label as a function of the identified marker of the user and correlations of each of the plurality of marker to a respective disorder state label in the first training data;

determining, by the computing device, as a function of the disorder state label, an aliment instruction set containing an edible program, wherein determining further comprises:

generating an aliment machine-learning model, wherein generating the aliment machine-learning model comprises:

training the aliment machine-learning model according to a second training set correlating each of a plurality of disorder state labels to a respective aliment instruction set such that the trained aliment machine-learning model is configured to receive the disorder state label as an input and output the edible program as a function of the disorder state label and correlations of each of the plurality of assigning a respective impact score for each provider alimentary possibility of a plurality of provider alimentary possibilities; and generating, by the computing device, an arranged list of provider aliment possibilities from a plurality of aliment possibilities as a function of the aliment instruction set and each respective impact score for each respective provider alimentary possibility of the plurality of provider alimentary possibilities; and representing, by the computing device, the arranged list on a display.

12. The method of claim 11, wherein receiving the input further comprises:
representing, a plurality of autoimmune disorders; and
obtaining, a user input relating to the plurality of autoimmune disorders.

13. The method of claim 11, wherein receiving the input further comprises identifying the autoimmune disorder as a function of the marker.

14. The method of claim 11, wherein identifying the marker further comprises:
obtaining, physiological data associated with the marker;
generating, an autoimmune machine-learning process using a third training set, the third training set relating physiological data associated with markers to an autoimmune databank; and
generating the autoimmune databank as a function of the autoimmune machine-learning process.

15. The method of claim 11, wherein the disorder state labels specifies an active autoimmune disorder.

16. The method of claim 11, wherein the disorder state label specifies a likelihood for an autoimmune disorder.

17. The method of claim 11, wherein the edible program further comprises a mutable edible program.

18. The method of claim 11, wherein the edible program further comprises a treatment edible program.

19. The method of claim 11, further comprising:
obtaining an aliment sequence from the arranged list; and
generating an updated arranged list as a function of a user preference.

20. The method of claim 19, further comprising:
determining an updated aliment instruction set; and
generating the updated arranged list as a function of the updated aliment instruction set.

* * * * *